United States Patent [19]

Nishikawa et al.

[11] Patent Number: 5,591,155
[45] Date of Patent: Jan. 7, 1997

[54] DISPOSABLE TRAINING PANT HAVING IMPROVED STRETCHABLE SIDE PANELS

[75] Inventors: Masaharu Nishikawa, Akashi; Keith W. Rollag, Ashiya, both of Japan; David M. Sageser, Cincinnati, Ohio; Jiro Yamada, Kobeshi, Japan

[73] Assignee: The Procter & Gamble Company, Cincinnati, Ohio

[21] Appl. No.: 597,552

[22] Filed: Feb. 2, 1996

Related U.S. Application Data

[63] Continuation of Ser. No. 338,609, filed as PCT/JP93/04036, Apr. 29, 1993, abandoned.

[30] Foreign Application Priority Data

May 22, 1992 [JP] Japan ..................... 4-155637

[51] Int. Cl.⁶ .................................................. A61F 13/16
[52] U.S. Cl. ........................................ 604/393; 604/385.2
[58] Field of Search .............................. 604/393, 385.1, 604/385.2, 373

[56] References Cited

U.S. PATENT DOCUMENTS

| | | | |
|---|---|---|---|
| 4,205,679 | 6/1980 | Repke et al. ............................ | 128/287 |
| 4,355,425 | 10/1982 | Jones et al. ............................. | 2/402 |
| 4,610,680 | 9/1986 | La Fleur ................................. | 604/385 |
| 4,610,681 | 9/1986 | Strohbeen et al. ..................... | 604/396 |
| 4,619,649 | 10/1986 | Roberts .................................. | 604/396 |
| 4,641,381 | 2/1987 | Heran et al. ............................ | 2/400 |
| 4,690,681 | 9/1987 | Haunschiled et al. ................. | 604/396 |
| 4,710,189 | 12/1987 | Lash ....................................... | 604/385 |
| 4,743,239 | 5/1988 | Cole ....................................... | 604/385 |
| 4,743,241 | 5/1988 | Igaue et al. ............................ | 604/385 |
| 4,834,741 | 5/1989 | Sabee ..................................... | 604/385.2 |
| 4,940,464 | 7/1990 | Van Gompel et al. ................. | 604/396 |
| 5,021,051 | 6/1991 | Hiuke ..................................... | 604/385.2 |
| 5,151,092 | 9/1992 | Buell et al. ............................. | 604/385.2 |
| 5,236,430 | 8/1993 | Bridges .................................. | 604/396 |
| 5,246,433 | 9/1993 | Hasse et al. ............................ | 604/396 |
| 5,358,500 | 10/1994 | LaVon et al. .......................... | 604/385.2 |

FOREIGN PATENT DOCUMENTS

| | | | |
|---|---|---|---|
| 0323040 | 5/1989 | European Pat. Off. ............ | 604/385.1 |
| 0320991 | 6/1989 | European Pat. Off. ............ | 604/385.1 |
| 0638304A1 | 2/1995 | European Pat. Off. ........ | A61F 13/64 |
| 0641552A1 | 3/1995 | European Pat. Off. ........ | A61F 13/15 |
| 1144674 | 3/1969 | United Kingdom ............. | A41B 9/04 |
| 2244909 | 12/1991 | United Kingdom ............. | A61F 13/15 |
| WO93/17648 | 9/1993 | WIPO ............................... | A61F 13/15 |
| WO93/24085 | 12/1993 | WIPO ............................... | A61F 13/15 |
| WO94/28845 | 12/1994 | WIPO ............................... | A61F 13/15 |
| WO95/03765 | 2/1995 | WIPO ............................... | A61F 13/15 |
| WO95/06451 | 3/1995 | WIPO ............................... | A61F 13/15 |

OTHER PUBLICATIONS

Zuikou, Incomplete Translation of Hei3–176 053 published Jul. 1991 pp. 1–7.

*Primary Examiner*—Robert A. H. Clarke
*Attorney, Agent, or Firm*—Kevin C. Johnson; Steven W. Miller; Jacobus C. Rasser

[57] ABSTRACT

The present invention provides a disposable training pant having an improved elasticized side panel which gives improved fit and comfort. The disposable diaper has an absorbent core chassis (30) and a pair of elasticized side panels (50) connected to the longitudinal sides of the chassis, where each side panel is formed of two elasticized laminate members (10), joined by a side seam along a non-elasticized outboard edge (52) of each member.

1 Claim, 5 Drawing Sheets

DISPOSABLE TRAINING PANT HAVING IMPROVED STRETCHABLE SIDE PANELS

This is a continuation of application Ser. No. 08/338,609, filed as PCT/JP93/04036 on Apr. 29, 1993, now abandoned.

FIELD OF THE INVENTION

The present invention related to disposable absorbent articles, more particularly to disposable absorbent diapers and incontinent products, and most particularly to disposable training pants and pull-on diaper. The invention is directed particularly to such articles and products, especially training pants, which have an elasticized side panel that provides the training pant with improved fit and comfort. As used herein, "training pant" includes also pull-on diapers comprising an absorbent core.

DESCRIPTION OF RELATED ART

Training pants have become popular, especially for use on toilet-training children. In the past some training pants have been made elastically extensible using elastic elements disposed in the training pants such that the waist opening and leg openings are at least partially encircled with elasticized bands. This method of using elastic elements is shown in U.S. Pat. No. 4,205,679 to Repke, et al.; U.S. Pat. No. 4,610,680 to LaFleur; U.S. Pat. No. 4,610,681 to Strohbeen, et al.; U.S. Pat. No. 4,641,381 to Heran, et al.; U.S. Pat. No. 4,909,804 to Douglas, Sr.; and U.S. Pat. No. 4,960,414 to Meyer.

Another method of elasticizing disposable training pants is shown in U.S. Pat. Nos. 4,490,464; 4,938,753; and 4,938,757 all of which issued to Van Gompel, et al. These patents disclose a pant-like garment formed by attaching discrete stretchable members to the side edges of the main body of the garment. The discrete stretchable members are described as being made by stretching an elastic or stretchable layer to a selected elongation, placing a nonstretchable layer, such as a nonwoven, on the stretched layer, bonding the layers together, and allowing the layers to relax so that the nonstretchable layer is gathered.

Other methods for making a stretchable member is described in U.S. Pat. No. 4,107,364, issued to Sisson on Aug. 15, 1978, U.S. Pat. No. 4,209,563 issued to Sisson on Jun. 24, 1980, U.S. Pat. No. 4,525,407 issued to Ness on Jun. 25, 1985, U.S. Pat. No. 4,834,741 issued to Sabee on May 30, 1989, European Patent Publication 409,315. The Procter & Gamble Company, published Jan. 23, 1991, all hereby incorporated by reference.

Still other methods for making a stretchable member is described in U.S. patent application Ser. Nos. 07/662536, 07/662537, and 07/662543, each filed Feb. 28, 1991 and assigned to The Procter & Gamble Company. These references describe making an elasticized laminate by mechanically stretching a zero-strain stretch laminate web to impart the elasticity thereto in the direction of stretching, at least up to the point of initial stretching. An elongatable, non-elastic nonwoven layer is first bonded to a liquid-impervious elastic layer while in its relaxed state to form the laminate web. The laminate web is then fed between a pair of opposed pressure applicators, preferably ones having three-dimensional surfaces which are complimentary to a varying degree with one another, and subjected to incremental mechanical stretching (or nonuniform or sequential mechanical stretching, as desired), whereby the elongatable nonwoven is permanently elongated in the direction of stretching. When the mechanical stretching is removed, the elastic layer will enable the laminate to return substantially to its pre-stretch shape and dimensions, thereby rendering the non-elasticized laminate elastically extensible in the direction of initial stretching.

While the elasticized zero-strain stretch laminates described above are useful for making elasticized, stretchable side panels for training pants, they are not completely satisfactory. The elongatable non-elastic nonwoven layer of the laminate can be torn at least partially along lines oriented in the machine direction of the web, and perpendicular to the direction of stretch. The at least partial tearing of the nonwoven can diminish the contribution of the nonwoven to the tensile strength of the laminate. Furthermore, the elastic layer itself generally has low tensile strength and low tear propagation resistance. This property can be problematic when the elasticized laminate is used as a side stretch panel on a training pant to achieve stretch in the lateral (front-to-back) direction of the training pant while being worn, since the lines of at least partial tearing of the nonwoven of the laminate are then oriented in the longitudinal (machine) direction. Futher, since the side seam is most preferably made in the longitudinal (machine) direction of the training pant (in order to optimize manufacturing speed and efficiency), the side seam can partially tear prematurely (for example, while the child is active) along the seam where the process for forming the side seam itself can further damage to some extent either the nonwoven or the elastic layer of the laminate. or both, along one or more of the lines of at least partial tearing of the nonwoven.

SUMMARY OF THE INVENTION

Though the problem may be solved by various means, none are completely satisfactory. For example, additional materials could be added to or between the front and the back edge portions of the side panels to make the seam stronger and to reduce damage to the elastic layer. However, the inventors have found that the problem can be solved by modifying the method for making the elasticized laminate used to form the elasticized side panels. During the making of the elasticized laminate, discrete and spaced apart regions of the laminate which is fed between the opposed pressure applicators are subjected to no or reduced mechanical stretching. After the laminate has been mechanically stretched, it is cut along its width (in the direction of feeding) in the middle of the regions where no or reduced mechanical stretching occurred (hereinafter referred to as "non-stretched region"). The widths of laminate are then cut to the appropriate lengths for front and back elasticized members. The non-stretched region is used as the respective outboard edge portions of the front and back elasticized members which are then joined to form the side seam. Thus, the present invention provides a side seam that has substantially improved strength and tear resistance, and provides a training pant with elasticized side panels having improved side seam integrity.

DETAILED DESCRIPTION OF THE INVENTION

Figure 1:
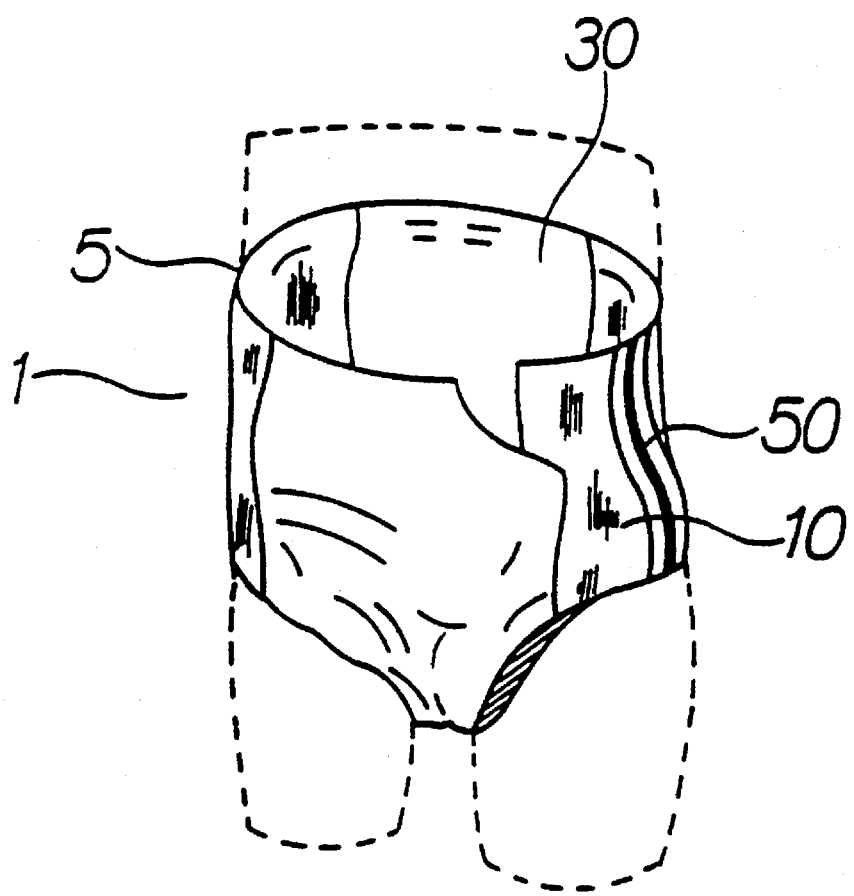
FIG. 1 is a schematic view of a training pant according to the present invention.

Practice of the present invention involves the making of a training pant 1 (FIG. 1) comprising the steps of: making of the elasticized members having a non-mechanically stretched outboard edge portion, making of the absorbent chassis, attaching the elasticized members to the edges of the absorbent chassis, and forming the side seam between the non-elasticized outboard edge portions of the elasticized members to form the training pant with elasticized side panels.

The elasticized members are generally made by: laminating into a laminate web at least one elongatable, non-elastic nonwoven layer with a elastic layer while in its relaxed state; mechanically stretching portions along the width of the laminate web to impart elasticity thereto in the direction of stretching, at least up to the point of initial stretching, thereby leaving other regions of non-elasticized stretched laminate; and cutting the resultant elasticized laminate web along its width and its length to form the individual front waist area and back waist area elasticized members of the side panel.

The absorbent chassis is generally made by placing an absorbent core between a liquid-impervious backsheet and a liquid-pervious topsheet. The absorbent chassis of the present invention is generally of a rectangular shape, having side edges and end edges, and a front and a back waist area.

The elasticized members are then attached along the side edges in the front waist area and the back waist area of the chassis, so that a portion of the non-mechanically stretched region of the elasticized member is the outboard edge portion thereof.

Finally, the absorbent chassis with the elasticized members attached is folded at approximately the longitudinal center, bringing the body-side face (topsheet face) of the front waist area into proximity with the body-side face of the back waist area. The body side surfaces of the non-mechanically stretched edge portions of the opposed elasticized members attached to the front and back waist areas are then joined with a heat seal, thereby completing the training pant.

An elasticized member 10 is generally made by: laminating into a laminate wed 11 at least one elongatable, non-elastic nonwoven layer 12 with at least one elastic layer 13 while both are in their relaxed state: mechanically stretching portions along the width of the laminate web 11 to impart elasticity thereto in the direction of stretching, at least up to the point of initial stretching, thereby leaving other regions of non-elasticized laminate: and cutting the resultant stretch laminate web 14 along its width and along its length, to form the individual front waist area and back elasticized members 10 of the side panel 5.

A typical example of the elongatable, non-elastic nonwoven layer 12 comprises a hydrophobic, nonwoven carded web having a basis weight in the range of about 30–37 grams per square meter and comprised of approximately 1–5 denier fibers, available from Hercules, Inc., U.S.A.

The elastic layer 13 can be liquid pervious or liquid impervious, such as with a spunbonded polymeric non-woven or a plastic film. A typical example of the elastic layer 13 comprises a polyurethane having a no-load caliper or thickness of approximately 0.045 mm (2 mil). An example includes DS-320C made by Japan Synthetic Rubber K.K.

The non-elastic nonwoven layer and the elastic layer are brought together and bonded to form the laminate 11. The adhesive to bond the layers can be applied as a uniform continuous layer of adhesive, a patterned layer of adhesive, or an array of separate lines, spirals, or slots of adhesive. In a preferred embodiment, the adhesive selected is stretchable and the glue applicator comprises a melt blown application system, such as Model No. GM-50-2-1-GH available from J&M Laboratories of Gainesville, Ga., U.S.A. employing a nozzle having 8 orifices per linear centimeter (20 orifices per linear inch), as measured in the cross-machine direction, each orifice measuring about 0.5 mm (0.020 inches) in diameter. A preferred adhesive is HM-6515 Hot Melt Adhesive, available from H. B. Fuller Company of St. Paul, Minn., U.S.A. The adhesive is heated to a temperature of about 170 degrees centigrade and applied at a rate of about 0.75–1.25 milligrams per square centimeter. Heated compressed air at a temperature of about 220 degrees centigrade and a pressure of about 2500 mm Hg gauge is issued through the secondary orifices in the nozzle to assist in uniform distribution of the adhesive fibrils during the laydown operation.

Figure 2:
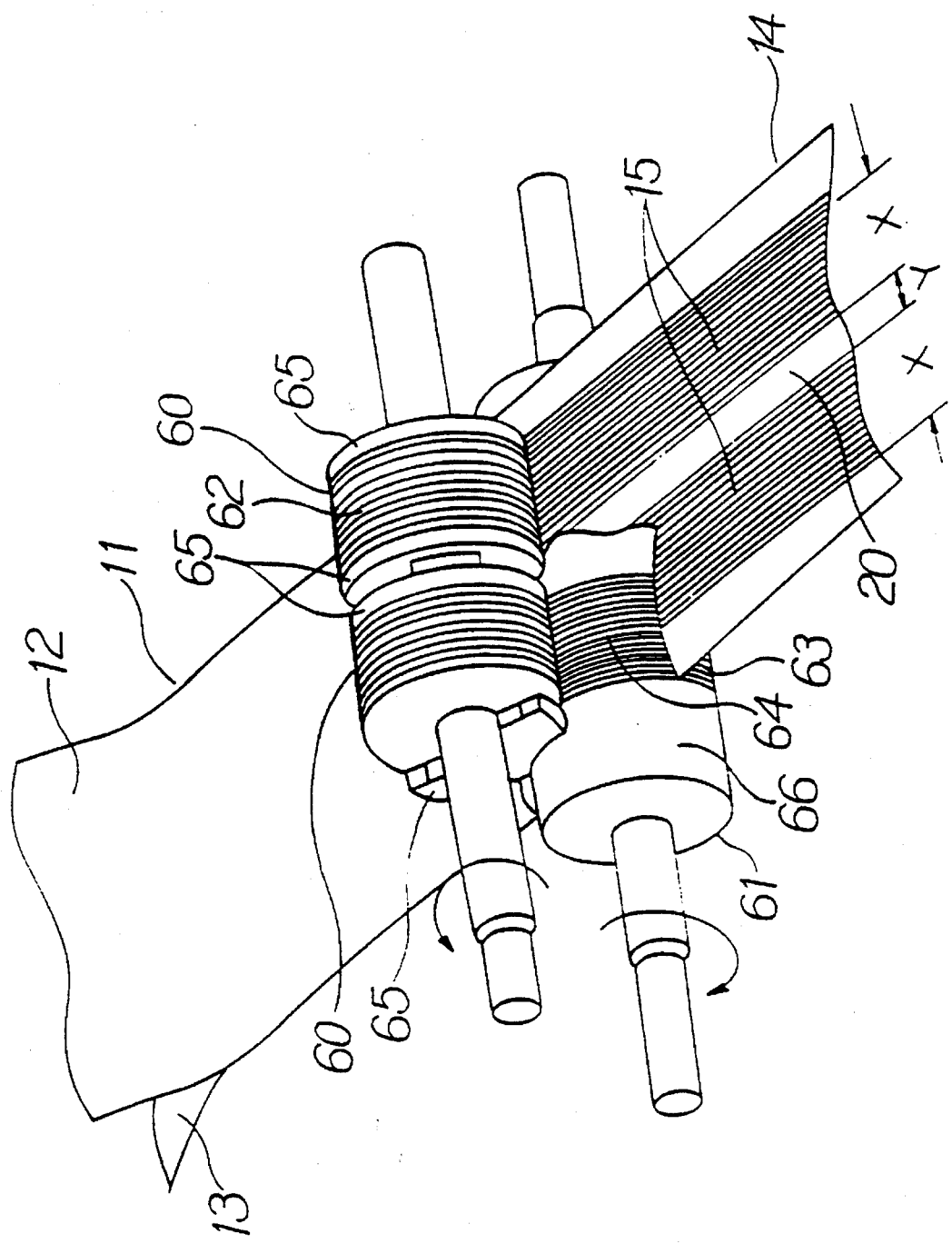
FIG. 2 is an explanatory view showing an apparatus for preventing contraction of a web used in the present invention.
Figure 3:
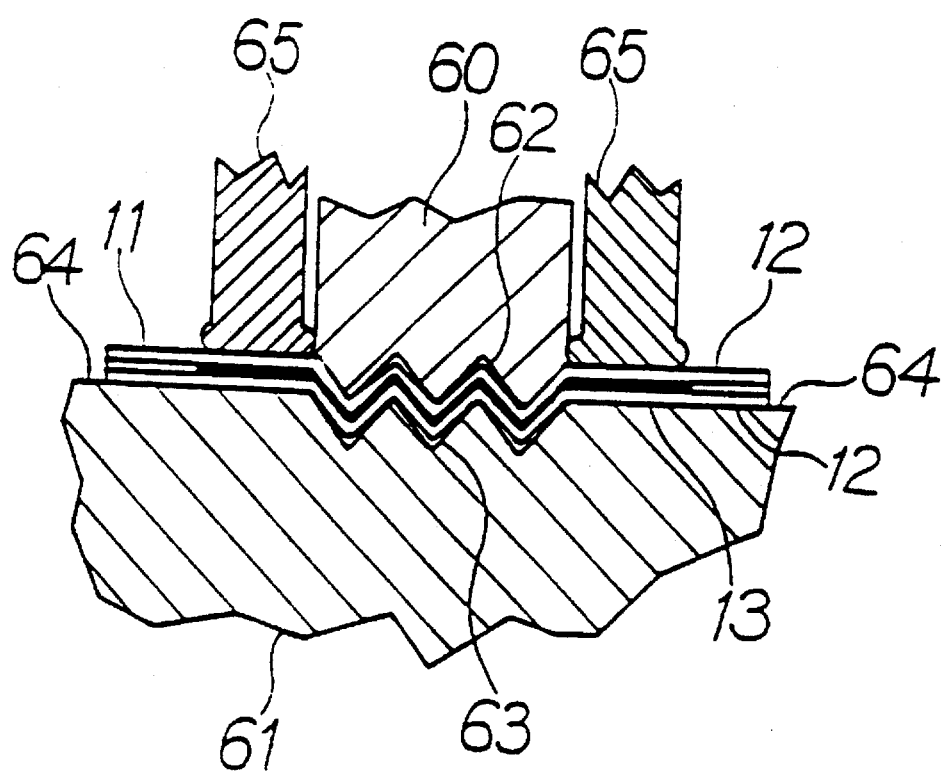
FIG. 3 is an explanatory view snowing the matching condition of upper corrugated rolls 60 and lower corrugated rolls 61 in the apparatus shown in FIG. 2.

As generally shown in FIG. 2, the laminate 11 web is then mechanically stretched to provide along the width of the wed regions 15 of elasticized laminate and regions 20 of non-stretched, non-elasticized laminate. Typically, a web of approximately 1 meter in width W is fed through the stretching apparatus at a time. An apparatus for mechanical stretching the zero-strain stretch laminate 11 can consist of upper corrugated rolls 60 and lower corrugated rolls 61 which are matched so that the respective corrugations can mesh (as further shown in FIG. 3). The region 15 of the web which has passed through and between the upper and lower corrugated rolls is mechanically stretched in the areas between the grooves 62 of the upper corrugated roll 60 and the grooves 63 of the lower corrugated roll 61. The regions 20 of the web which has passed between side-by-side upper corrugated rolls 60 do not receive any mechanical stretching.

It is preferred to use a means of clamping the web just outside the respective regions of mechanical stretching in order to prevent the web from contracting in a direction parallel to the direction of stretching as the web passes between the meshed rolls. A suitable means of preventing such contraction is shown in FIG. 2, where compressible disks 65 having a slightly larger diameter than the diameter of the upper corrugated rolls 60 are mounted adjacent each side of the grooves portions of line upper corrugated rolls. The compressible disks tightly grid line web and hold it securely against the coinciding non-grooved portions 64 of the lower corrugated roll 61.

Figure 4:
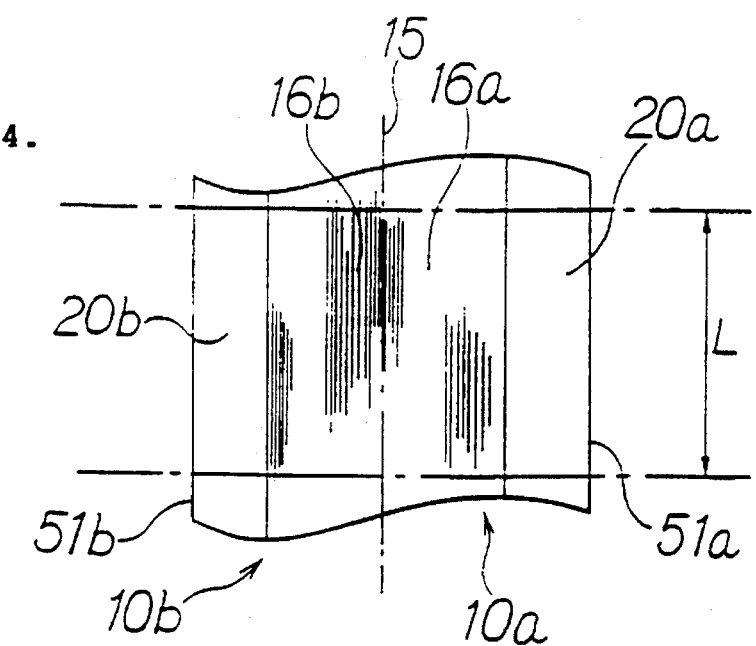
FIG. 4 is an explanatory view showing how the web is cut into two elasticized members with an angle.

In the present invention, the regions 15 of mechanical stretching and the regions 20 of non-stretching will alternate along the width of the web. The width of the region 15 to be mechanically stretched (shown as X) is selected based on the desired waist opening of the training pant and the degree of elasticity of the stretch laminate, as well as on how the processed web 14 is cut after stretching into the individual side elasticized members 10. For example, the processed web 14 can be cut, such as with knives, along its width at approximately the center of each of the regions 20 of non-mechanical stretching. Then as shown in FIG. 4, each individual width of processed laminate can further be cut into half substantially in the center of the region of mechanical stretching, and cut into individual lengths L along the length of the web, to form sets of first side 10a and second side 10b elasticized members for attachment to the absorbent chassis and forming of the side seam. Depending on the size of the training pant to be made, the width X can be from 60–140 mm. For example, for a Large training pant intended for use by a child weighing from about 9–14 kg, the width X is about 70–100 mm, more preferably from 74–80 mm. In a particularly preferred embodiment, the width X is about 78 ram. Thus, after having cut the individual lengths of web in about the center of the region X, the width of the elasticized laminate portion 16 of an individual side elasticized member of this embodiment will be from about 30–70 mm. For the aforementioned Large training pant, the width X is from about 35–50 mm, more preferably from 37–40 mm, and particularly about 39 mm.

Preferably, the width of a region 20 of non-mechanical stretching of the web (shown as Y) will be from about 20–120 mm. For the aforementioned Large training pant, the width Y is about 20–60 mm, more preferably from 40–56 mm, and particularly about 50 mm. Since the web is cut in the center of the region Y in making the individual widths of web, the width of the non-mechanically stretched outboard edge portion 51 of the elasticized member is about 10–60 mm, and for the aforementioned Large training pant, Y is about 10–30 mm, more preferably from 20–28 mm, and particularly about 25 mm.

Preferable the length L of each elasticized member is from about 50–190 mm. As with the other dimensions of the elasticized members, the length L selected will depend on the size of the intended wearer, and fit and comfort considerations. For the aforementioned Large training pant, the length L is from about 80–170, more preferably from about 100–160 mm.

The absorbent chassis 30 is generally made by placing an absorbent core 31 between a liquid-impervious backsheet 32 and a liquid-pervious topsheet 33. The absorbent chassis of the present invention is generally of a rectangular shape, having side edges 35a, 35b and end edges 36a, 36b, and a front waist area 40 and a back waist area 41.

The absorbent core 31 can be any absorbent means which is generally compressible, conformable, non-irritating to the wearer's skin, and capable of absorbing and retaining liquids such as urine and other certain body exudates. The absorbent core has a garment surface, a body surface, side edges, and waist edges. The absorbent core may be manufactured in a wide variety of sizes and shapes (e.g., rectangular, hourglass, "T"-shaped, asymmetric, etc.) and from a wide variety of liquid-absorbent materials commonly used in disposable diapers and other absorbent articles such as comminuted wood pulp which is generally referred to as airfelt. Examples of other suitable absorbent materials include creped cellulose wadding, meltblown polymers including cross-linked cellulosic fibers, tissue including tissue wraps and tissue laminates, absorbent foams, absorbent sponges, superabsorbent polymers, absorbent gelling materials, or any equivalent material or combinations of materials. The configuration and construction of the absorbent core may also be varied (e.g., the absorbent core may have varying caliper zones, a hydrophilic gradient, a superabsorbent gradient, or lower average density and lower average basis weight acquisition zones; or may comprise one or more layers or structures). The total absorbent capacity of the absorbent core should, however, be compatible with the design loading and the intended use of the diaper. Further, the size and absorbent capacity of the absorbent core may be varied to accommocdate wearers ranging from infants through adults.

In one embodiment of the present invention, the absorbent core 31 comprises two distinct webs or layers comprising an acquisition/distribution core and a storage core (neither shown). The acquisition/distribution core is positioned between the topsheet and the storage core, and the storage core is positioned between the acquisition/distribution core and the backsheet. The acquisition/distribution core has a top surface area which preferably is from 15%–170% of the top surface area of the storage core. The acquisition/distribution core is preferably positioned relative to the storage core so that none of its surface area extends beyond the boundaries of the storage core. The acquisition/distribution core preferably comprises a web of chemically stiffened cellulosic fibers, although binding means such as non-stiffened cellulosic fibers, synthetic fibers, chemical additives, and thermoplastic fibers can be added to increase the physical integrity of the web. The storage core preferably comprises an airlaid web of superabsorbent material and fiber material, preferably airfelt. Optionally, and most preferably, a pervious sheet (e.g., a tissue sheet) or other scrim may be positioned between the acquisition/distribution core and the storage core to increase the integrity of the absorbent core during processing and/or use.

The acquisition/distribution core serves to quickly collect discharged body fluids, to quickly transport the fluid from the point of initial contact to other parts of the acquisition/distribution core, and to temporarily hold such discharged body fluids until they can be absorbed by the storage core. The distribution function of the acquisition/distribution core is of particular importance in order to more fully utilize the capacity of the storage core. Thus, while the acquisition/distribution core may comprise a wide variety of absorbent materials, it preferably comprises fiber material that can rapidly transport fluid and not collapse upon being wetted so that the acquisition/distribution core can effectively acquire and distribute second and successive voids of fluid as well as utilize a minimal amount (<2%) of superabsorbent material (due to The slowness of their uptake and gel blocking).

The backsheet 32 is impervious to liquids (e.g., urine) and is preferably manufactured from a thin plastic film, although other flexible liquid impervious materials may also be used. As used herein, the term "flexible" refers to materials which are compliant and will readily conform to the general shape and contours of the human body. The backsheet prevents the exudates absorbed and contained in the absorbent core from wetting articles which contact the diaper such as bedsheets and undergarments. The backsheet may thus comprise a woven or nonwoven material, polymeric films such as thermoplastic films of polyethylene or polypropylene, or composite materials such as a film-coated nonwoven material. Preferably, the backsheet is a thermoplastic film having a thickness of from about 0.012 mm (0.5 mil) to about 0.051 mm (2.0 mils).

The backsheet 32 is positioned adjacent the garment surface of the absorbent core and is preferably joined thereto by attachment means such as those well known in the art. For example, the backsheet may be secured to the absorbent core by a uniform continuous layer of adhesive, a patterned layer of adhesive, or an array of separate lines, spirals, or spots of adhesive. Adhesives which have been found to be satisfactory are manufactured by Century Adhesives, Inc. of Columbus, Ohio and marketed as Century 5227; and by H. B. Fuller Company of St. Paul, Minn. and marketed as HL-1258. The attachment means will preferably comprise an open pattern network of filaments of adhesive as is disclosed in U.S. Pat. No. 4,573,986 entitled "Disposable Waste-Containment Garment", which issued to Minetola and Tucker on Mar. 4, 1986, and which is incorporated herein by reference. An exemplary attachment means of an open pattern network of filaments comprises several lines of adhesive filaments swirled into a spiral pattern such as is illustrated by the apparatus and methods shown in U.S. Pat. No. 3,911,173 issued to Sprague, Jr. on Oct. 7, 1975; U.S. Pat. No. 4,785,996 issued to Ziecker, et al. on Nov. 22, 1978; and U.S. Pat. No. 4,842,666 issued to Werenicz on Jun. 27, 1989. Each of these patents are incorporated herein by reference. Alternatively, the attachment means may comprise heat bonds, pressure bonds, ultrasonic bonds, dynamic mechanical bonds, or any other suitable attachment means or combinations of these attachment means as are known in the art.

The topsheet 33 is compliant, soft feeling, and non-irritating to the wearer's skin. Further, the topsheet 33 is liquid pervious permitting liquids (e.g., urine) to readily penetrate through its thickness. A suitable topsheet can be manufactured from a wide range of materials, such as porous foams; reticulated foams; apertured plastic films; or woven or nonwoven webs of natural fibers (e.g., wood or cotton fibers), synthetic fibers (e.g., polyester or polypropylene fibers), or a combination of natural and synthetic fibers. Preferably, the topsheet is made of a hydrophilic or a surfactant-treated hydrophobic material.

The topsheet 33 is positioned adjacent the body surface of the absorbent core and is preferably joined thereto and to the backsheet 32 by attachment means (not shown) such as those well known in the art. Suitable attachment means are described with respect to joining the backsheet to the absorbent core. As used herein, the term "joined" encompasses configurations whereby an element is directly secured to the other element by affixing the element directly to the other element, and configurations whereby the element is indirectly secured to the other element by affixing the element to intermediate member(s) which in turn are affixed to the other element. In a preferred embodiment of the present invention, the topsheet and the backsheet are joined directly to each other in the diaper periphery and are indirectly joined together by directly joining them to the absorbent core by the attachment means.

Figure 6:
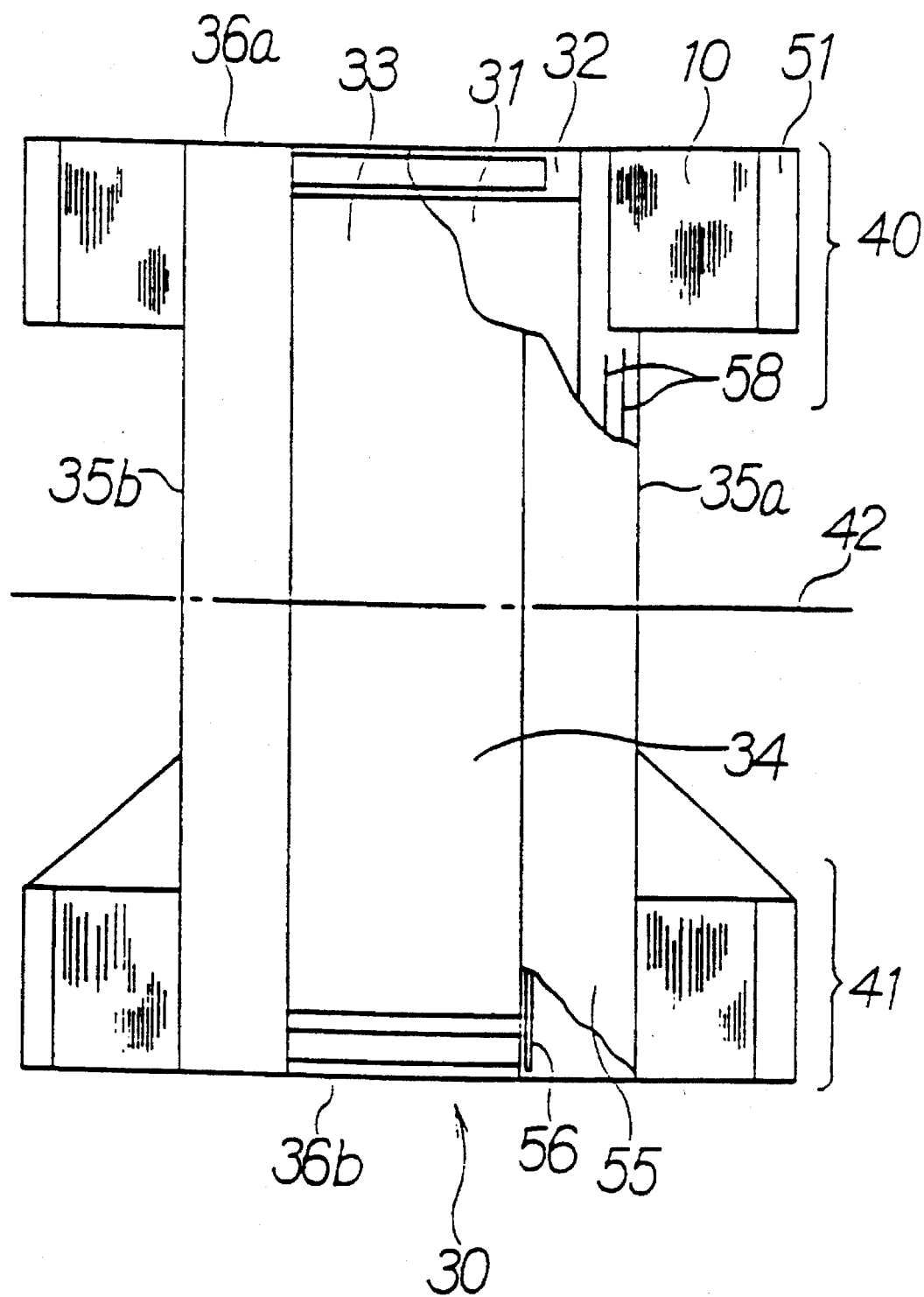
FIG. 6 is an explanatory view showing how the elasticized member s attached between the backsheet and the cuff.

The elasticized members 10 are then attached to the front waist area 40 and the back waist area 41 on each side edge 35a, 35b of the chassis, so that the non-mechanically stretched outboard edge portion 51 thereof is the distal edge. The inboard attachment edge 17 of the elasticized member 10 is preferably attached to the absorbent chassis 30 between the topsheet 33 and the backsheet 32 by means of an adhesive 18 applied to either surface, preferably both surfaces, of the inboard attachment edge 17. The inboard attachment edge 17 of the elasticized member can alternatively be attached between the backsheet and other structures or layers of material in the chassis; for example, as shown in FIG. 6, between the backsheet and an inboard elasticized barrier leg cuff 55. Generally, the width of the attachment edge 17 inserted and attached between the topsheet and backsheet is from about 5–20 mm, more preferably from about 10–15 mm. The adhesive can be applied in any effective means, such as continuously, intermittently, in either a straight or curved line, or in a swirl pattern.

Figure 5:
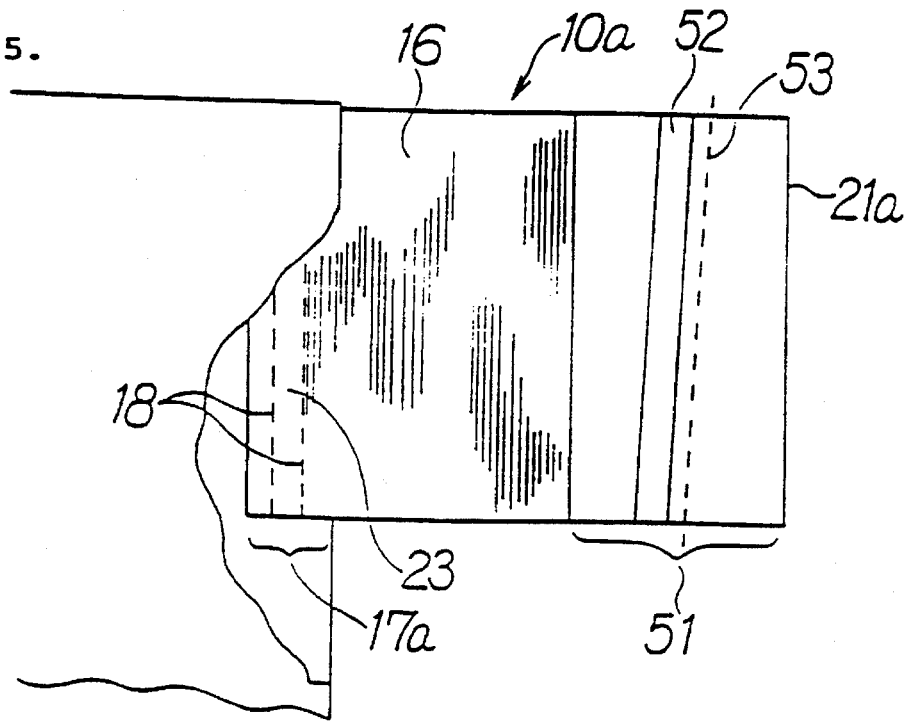
FIG. 5 is an explanatory view showing how the seat is attached to the elasticized members with an angle.

Finally, the absorbent chassis 30 with the elasticized members 10 attached is mechanically folded at approximately the longitudinal center 42, thereby bringing the body-side face 34 of the front waist area 40 into proximity with the body-side face of the back waist area 41. The body-side facing surfaces of the outboard edge portions 51 of the opposed elasticized members 10 attached to the front and back waist areas are then joined with a seal 52, thereby forming an elasticized side panel 5 and completing the training pant. The seal 52 can be made parallel with the longitudinal side 35 of the absorbent chassis, or can be angled slightly, as shown in FIG. 5. The seal 52 is preferably made as thin as possible to minimize the width of the Side seam 50 formed. A preferred seal is a pressure bond seal which bonds together the elastic layers 13 of the respecting outboard edge portions 51 of the laminates. In a preferred method, the seal 52 is made by passing the outboard edge portions between a rotating anvil roll and a rotating pressure roll which typically exert about 1500–5000 kilograms force per square centimeter pressure on the laminae, thereby forming a line of seal 52 having a width generally from 1–10 mm, preferably from 2–5 mm. The bonding pattern can be continuous or intermittent, and straight, curved, or irregular. Preferably, a temperature below about 80 degrees centigrade is used. It is most preferred to operate the anvil and pressure roll at their ambient temperature. A higher temperature can be used so long as it is well below the thermoplastic melting temperature of the material of the elastic layer and so long as the elastic layer itself is not damaged or weakened at such temperatures. Thus, the pressure, temperature, bond pattern and duration of application of the sealing means is selected to optimize the welding of the polymeric materials of the respective elasticized layer of the laminates without deteriorating the laminate or its components. The side seam 50 can also be made by other sealing means known in the art, including ultrasonic sealing, heat sealing, and combinations thereof.

After the side seam 50 is made, the excess material outside of the seal can be trim cut away along a line 53 outboard of the seal 52. Further, portions of the side panels can be trim cut, particularly around the leg opening edge, to provide an improved fit and better comfort. The elasticized members 10 can be trim cut together immediately before or after seaming, or the front and back elasticized members can be trimmed separately prior to or after attachment to the absorbent chassis.

Optionally, the training pant of the present invention can comprise other features and structures commonly used in diapers and training pants. Such optional features include, but are not limited to: disposal tapes, elasticized waist and tummy panels in the back and front waist areas of the adsorbent chassis; elasticized outboard leg cuffs and elasticized inboard barrier leg cuffs, positioned generally along the sides of the absorbent chassis to partially surround and seal around the leg opening of the training pant; wetness indicators: and elasticized members in the crotch region of the absorbent chassis to provide better comfort, fit and containment of bodily exudates.

The effect of the present invention is to provide a training pant having elasticized side panels which have an improved side seam therein. The seam, such as one formed by a pressure sealing, is strong enough to remain sealed under ordinary use, yet can be easily torn by a person desiring to remove the training pant from the wearer, for example after the pant has been soiled.

We claim:

1. A disposable training pant comprising:
   1) an absorbent chassis having side edges and a front and a back waist area, comprising:
      a liquid-pervious topsheet,
      a liquid-impervious backsheet, and
      an absorbent core positioned between said topsheet and said backsheet; and 2) an elasticized side panel attached to and joining the front waist area and the back waist area along each longitudinal side of the absorbent chassis, said side panel being laterally stretchable, comprising:
  a front elasticized member and a back elasticized member, each comprising:
    (i) a non-elasticized laminate portion comprising at least one elongatable, non-elastic nonwoven layer and at least one elastic layer, said non-elasticized laminate portion forming an outboard edge and
    (ii) an elasticized laminate portion; and
  a side seam joining said outboard edges of said front elasticized member and said back elasticized member.

* * * * *